United States Patent
Hirata

(10) Patent No.: US 10,437,050 B2
(45) Date of Patent: Oct. 8, 2019

(54) PHASE-MODULATION-ELEMENT ADJUSTMENT SYSTEM AND METHOD FOR DECREASING WAVEFRONT ABERRATION

(71) Applicant: OLYMPUS CORPORATION, Tokyo (JP)

(72) Inventor: Tadashi Hirata, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 439 days.

(21) Appl. No.: 15/402,466

(22) Filed: Jan. 10, 2017

(65) Prior Publication Data

US 2017/0115180 A1    Apr. 27, 2017

Related U.S. Application Data

(63) Continuation of application No. PCT/JP2015/070328, filed on Jul. 15, 2015.

(30) Foreign Application Priority Data

Jul. 16, 2014 (JP) .................... 2014-145750

(51) Int. Cl.
G02B 27/00 (2006.01)
A61B 3/10 (2006.01)
(Continued)

(52) U.S. Cl.
CPC ........ G02B 27/0068 (2013.01); A61B 3/1015 (2013.01); G02B 21/0032 (2013.01);
(Continued)

(58) Field of Classification Search
CPC ........... G01M 11/0242; G02B 21/0032; G02B 27/0068; G02B 21/0068; G02B 21/0072;
(Continued)

(56) References Cited

U.S. PATENT DOCUMENTS

| 5,442,413 A | 8/1995 | Tejima et al. |
| 6,774,944 B1 | 8/2004 | Fukuyama |

(Continued)

FOREIGN PATENT DOCUMENTS

| EP | 2983027 A1 | 2/2016 |
| JP | H06-265814 A | 9/1994 |

(Continued)

OTHER PUBLICATIONS

International Search Report dated Oct. 20, 2015 issued in PCT/JP2015/070328.

*Primary Examiner* — Que Tan Le
*Assistant Examiner* — Jennifer D Bennett
(74) *Attorney, Agent, or Firm* — Scully, Scott, Murphy & Presser, P.C.

(57) ABSTRACT

A phase-modulation-element adjustment system including: a positional-relationship adjustment unit that is used for a laser-scanning confocal observation apparatus including a plurality of image-forming lenses for forming a final image and at least one intermediate image and a wavefront-disturbing element and a wavefront-restoring element being placed at positions between which any of the intermediate images formed by the image-forming lenses is disposed and having opposite phase characteristics to each other and that is capable of adjusting a relative positional relationship between the wavefront-disturbing element and the wavefront-restoring element; a wavefront-aberration measurement unit for measuring a wavefront aberration of light that has come from an object and that has passed through the wavefront-disturbing element and the wavefront-restoring element; and a processor for controlling the positional-relationship adjustment unit so that the wavefront aberration measured by the wavefront-aberration measurement unit decreases.

7 Claims, 4 Drawing Sheets

(51) Int. Cl.
  *G02B 21/00* (2006.01)
  *A61B 3/14* (2006.01)
(52) U.S. Cl.
  CPC ..... *G02B 21/0056* (2013.01); *G02B 21/0068* (2013.01); *G02B 21/0072* (2013.01); *G02B 21/0076* (2013.01); *A61B 3/14* (2013.01)
(58) Field of Classification Search
  CPC ............ G02B 21/0056; G02B 21/0076; G02B 27/0093; G01N 21/6458; G01N 2021/6463; A61B 3/14; A61B 3/1015
  See application file for complete search history.

(56) References Cited

U.S. PATENT DOCUMENTS

| | | | |
|---|---|---|---|
| 10,108,008 B2 * | 10/2018 | Fukuyama | G02B 13/22 |
| 2004/0150879 A1 | 8/2004 | Araki et al. | |
| 2004/0227101 A1 | 11/2004 | Iketaki et al. | |
| 2007/0046948 A1 * | 3/2007 | Podoleanu | A61B 3/102 356/497 |
| 2012/0140171 A1 * | 6/2012 | Hirose | A61B 3/1025 351/206 |
| 2013/0070217 A1 | 3/2013 | Tatsuno | |
| 2015/0146196 A1 * | 5/2015 | Huang | G01J 9/00 356/121 |
| 2016/0025970 A1 | 1/2016 | Fukuyama | |
| 2016/0209646 A1 * | 7/2016 | Hattori | G02B 21/06 |

FOREIGN PATENT DOCUMENTS

| | | |
|---|---|---|
| JP | H11-109243 A | 4/1999 |
| JP | 2004-239660 A | 8/2004 |
| JP | 2005-062155 A | 3/2005 |
| JP | 2006-311473 A | 11/2006 |
| JP | 2007-060647 A | 3/2007 |
| JP | 4011704 B2 | 11/2007 |
| JP | 2013-083817 A | 5/2013 |
| WO | WO 2014/163114 A1 | 10/2014 |
| WO | WO-2014163114 A1 * | 10/2014 ............ G02B 13/22 |

* cited by examiner

PHASE-MODULATION-ELEMENT ADJUSTMENT SYSTEM AND METHOD FOR DECREASING WAVEFRONT ABERRATION

CROSS-REFERENCE TO RELATED APPLICATIONS

This is a continuation of International Application PCT/JP2015/070328, with an international filing date of Jul. 15, 2015, which is hereby incorporated by reference herein in its entirety. This application claims the benefit of Japanese Patent Application No. 2014-145750, the content of which is incorporated herein by reference.

TECHNICAL FIELD

The present invention relates to a phase-modulation-element adjustment system and a phase-modulation-element adjustment method.

BACKGROUND ART

There is a known method for moving a focal position in a direction along the optical axis by adjusting the optical-path length at an intermediate-image position (refer to, for example, Patent Literature 1 below).

CITATION LIST

Patent Literature

PTL 1

Publication of Japanese Patent No. 4011704

SUMMARY OF INVENTION

Solution to Problem

The present invention provides the following solutions.

A first aspect of the present invention is a phase-modulation-element adjustment system including: a positional-relationship adjustment unit that is used for a microscope apparatus including a plurality of image-forming lenses for forming a final image and at least one intermediate image and two phase-modulation elements being placed at positions between which any of the intermediate images formed by the image-forming lenses is disposed and having opposite phase characteristics to each other and that is capable of adjusting a relative positional relationship between the two phase-modulation elements; a wavefront-aberration measurement unit for measuring a wavefront aberration of light that has come from an object and that has passed through the two phase-modulation elements; and a control unit for controlling the positional-relationship adjustment unit so as to decrease the wavefront aberration measured by the wavefront-aberration measurement unit.

A second aspect of the present invention is a phase-modulation-element adjustment method of a microscope apparatus, wherein a final image is formed by causing a first phase-modulation element to impart a spatial disturbance to a wavefront of light that comes from an object and that forms an intermediate image and by causing a second phase-modulation element to cancel out the spatial disturbance on the wavefront of the light that has formed the intermediate image, the method including: a measurement step of measuring wavefront aberration of the light that has from the object and that has passed through the two phase-modulation elements; and an adjustment step of adjusting a relative positional relationship between the two phase-modulation elements so as to decrease the wavefront aberration measured in the measurement step.

DESCRIPTION OF EMBODIMENTS

First Embodiment

A phase-modulation-element adjustment system and a phase-modulation-element adjustment method according to a first embodiment of the present invention will now be described with reference to the drawings.

Figure 1:
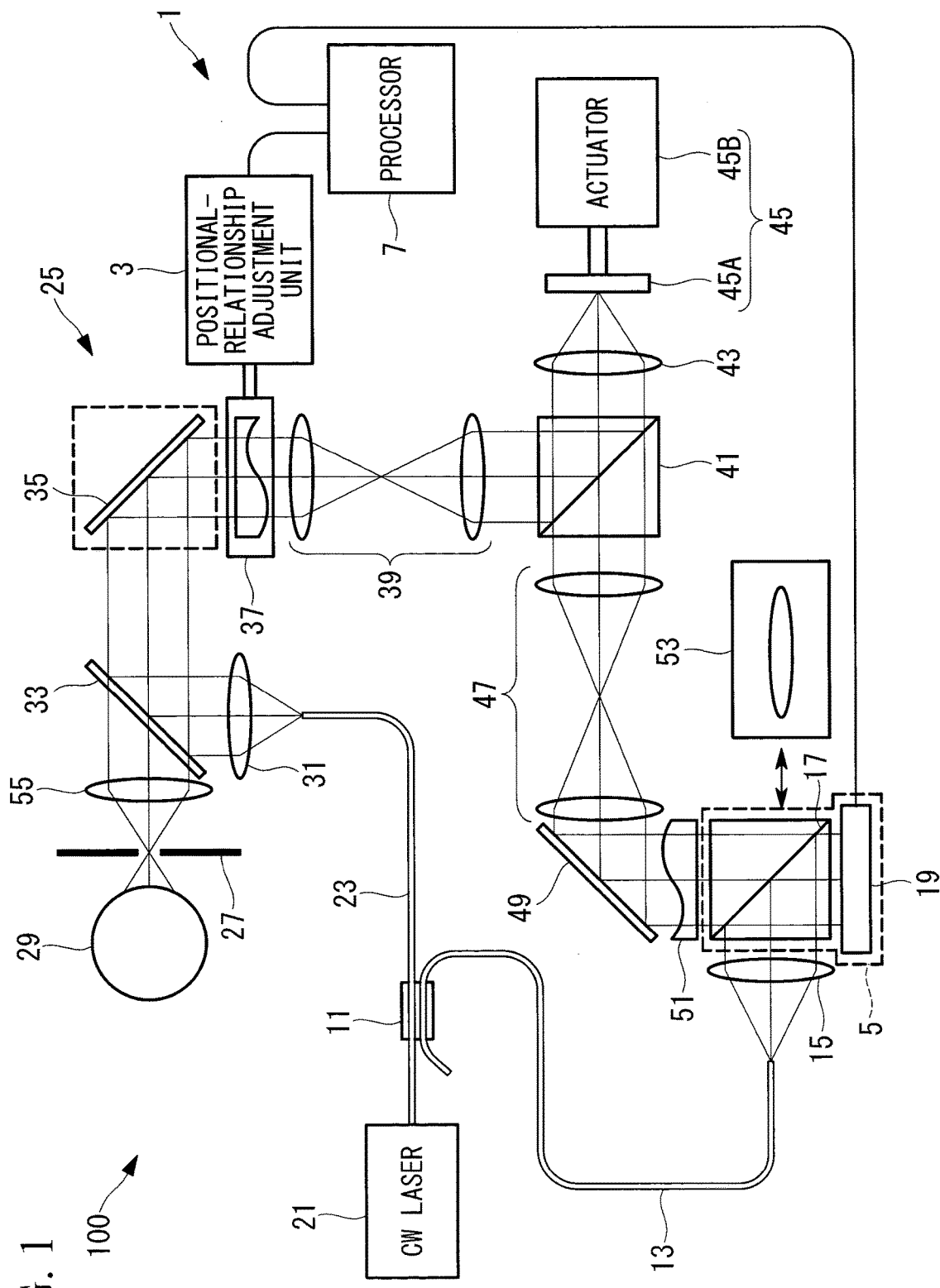
FIG. 1 is a schematic diagram depicting a phase-modulation-element adjustment system according to a first embodiment of the present invention.

A phase-modulation-element adjustment system 1 according to this embodiment is used in, for example, a laser-scanning confocal observation apparatus (microscope apparatus) 100 as shown in FIG. 1 and adjusts the phase modulation imparted by the use of a wavefront-disturbing element (phase-modulation element) 37 and a wavefront-restoring element (phase-modulation element) 51 of the laser-scanning confocal observation apparatus 100.

First, the laser-scanning confocal observation apparatus 100 will be described.

The laser-scanning confocal observation apparatus 100 includes: a CW laser (Continuous Wave laser, object) 21 for continuously producing a coherent laser beam; a single-mode optical fiber 23 for guiding the laser beam emitted from the CW laser 21 (hereinafter, referred to simply as "the optical fiber 23"); an image-forming optical system 25 that collects the laser beam guided by the optical fiber 23 to an examination object (object, not shown in the figure) and that collects the light from the examination object; a pinhole 27 for transmitting the fluorescence collected by the image-forming optical system 25; and a photodetector 29, like a photomultiplier tube, for detecting the fluorescence that has passed through the pinhole 27.

The image-forming optical system 25 includes: a collimating lens 31 for transforming the laser beam guided by the optical fiber 23 into collimated light; a dichroic mirror 33 that deflects the laser beam transformed into collimated light by the collimating lens 31 and transmits fluorescence from the examination object; a galvanometer mirror 35 for two-dimensionally scanning the laser beam deflected by the dichroic mirror 33; a wavefront-disturbing element 37 for imparting phase modulation to the wavefront of the laser beam scanned by the galvanometer mirror 35; and a pair of first intermediate-image forming lenses (image-forming lenses) 39 that focus the laser beam from the wavefront-disturbing element 37 to form an intermediate image.

The image-forming optical system 25 further includes: a half mirror 41 for deflecting the laser beam that has passed through the pair of first intermediate-image forming lenses 39; an intermediate-image forming lens (image-forming lens) 43 that focuses the laser beam deflected by the half mirror 41 and that forms an intermediate image; an optical-path-length changing unit 45 for reflecting and returning the laser beam focused by the intermediate-image forming lens 43; a pair of second intermediate-image forming lenses (image-forming lens) 47 that focus the laser beam returned by the optical-path-length changing unit 45 to form an intermediate image; a reflection mirror 49 for reflecting the laser beam that has passed through the pair of second intermediate-image forming lenses 47; a wavefront-restoring element 51 for imparting a phase modulation to the wavefront of the laser beam from the reflection mirror 49; an objective lens (image-forming lens) 53 that irradiates the examination object with the laser beam that has passed through the wavefront-restoring element 51 and collects the fluorescence produced at the examination object; an image-forming lens 55 that forms a final image by focusing the fluorescence collected by the objective lens 53 and returning along the optical path of the laser beam.

The galvanometer mirror 35 is placed in the vicinity of a position conjugate with the pupil of the objective lens 53. This galvanometer mirror 35 is configured of, for example, two mirrors that can swing about reciprocation axes orthogonal to each other.

The wavefront-disturbing element 37 is placed in the vicinity of the pupil position of the pair of first intermediate-image forming lenses 39. Furthermore, the wavefront-disturbing element 37 is composed of an optically transparent material that can transmit light, and when transmitting light, it imparts, to the wavefront of the light, a phase modulation in accordance with the uneven shape on its surface. In addition, the wavefront-disturbing element 37 has opposite phase characteristics to those of the wavefront-restoring element 51.

Therefore, when transmitting, for example, the laser beam from the CW laser 21, the wavefront-disturbing element 37 imparts a disturbance to the wavefront. In addition, when transmitting the fluorescence returning from the examination object via the wavefront-restoring element 51 along the optical path of the laser beam, the wavefront-disturbing element 37 imparts a phase modulation that cancels out the phase modulation imparted to the fluorescence wavefront by the wavefront-restoring element 51.

While reflecting the laser beam from the pair of first intermediate-image forming lenses 39 towards the intermediate-image forming lens 43, the half mirror 41 transmits, towards the pair of second intermediate-image forming lenses 47, the laser beam returning from the optical-path-length changing unit 45 via the intermediate-image forming lens 43.

The optical-path-length changing unit 45 includes: a plane mirror 45A placed at the intermediate-image forming plane resulting from the intermediate-image forming lens 43; and an actuator 45B for displacing the plane mirror 45A in the optical-axis direction. The plane mirror 45A is placed so as to be orthogonal to the optical axis of the intermediate-image forming lens 43.

This optical-path-length changing unit 45 changes the optical-path length between the intermediate-image forming lens 43 and the plane mirror 45A by displacing the plane mirror 45A in the optical-axis direction through the operation of the actuator 45B, thereby changing the focal position of the objective lens 53 in the examination object along the optical-axis direction. It is possible to acquire a plurality of images focused at different positions in the depth direction of the examination object by causing the optical-path-length changing unit 45 to move, along the optical-axis direction, the focal position of the objective lens 53 in the examination object and by acquiring images of the observation light at different focal positions.

The wavefront-restoring element 51 is placed in the vicinity of the pupil position of the objective lens 53. The wavefront-restoring element 51 is also composed of an optically transparent material that can transmit light and is configured to, when transmitting light, impart, to the light wavefront, a phase modulation in accordance with the uneven shape on its surface. As described above, the wavefront-restoring element 51 has opposite phase characteristics to those of the wavefront-disturbing element 37.

Therefore, when transmitting, for example, the laser beam entering from the CW laser 21 via the wavefront-disturbing element 37, the wavefront-restoring element 51 imparts, to the light wavefront, a phase modulation that cancels out the wavefront disturbance imparted by the wavefront-disturbing element 37. Furthermore, when transmitting the fluorescence from the examination object, it imparts a disturbance to the wavefront.

In the laser-scanning confocal observation apparatus 100 with the above-described structure, after the laser beam produced from the CW laser 21 is guided by the optical fiber 23 and is transformed into collimated light by the collimating lens 31, the laser beam is deflected by the dichroic mirror 33 and is then scanned two-dimensionally by the galvanometer mirror 35. Then, the laser beam passes through the wavefront-disturbing element 37, is deflected at the half mirror 41 via the pair of first intermediate-image forming lenses 39, is focused by the intermediate-image forming lens 43, and is returned by the plane mirror 45A of the optical-path-length changing unit 45.

The laser beam returned by the plane mirror 45A is reflected by the reflection mirror 49 after passing through the intermediate-image forming lens 43, the half mirror 41, and the pair of second intermediate-image forming lenses 47 and is radiated onto the examination object by the objective lens 53 after passing through the wavefront-restoring element 51.

After the disturbance is imparted to the wavefront of this laser beam as a result of the laser beam passing through the wavefront-disturbing element 37, the laser beam forms an intermediate image at the plane mirror 45A of the optical-path-length changing unit 45, hence causing the intermediate image to become unclear. Therefore, even if a foreign object, such as a flaw or dust, exists on the surface of the plane mirror 45A, an image of the foreign object can be prevented from overlapping the intermediate image. Furthermore, for the laser beam returned by the optical-path-length changing unit 45, the wavefront disturbance imparted by the wavefront-disturbing element 37 is canceled out as a result of the laser beam passing through the wavefront-restoring element 51. For this reason, a final image that has been made clear can be formed at the examination object. Furthermore, the image formation depth of the final image can be adjusted arbitrarily by the optical-path-length changing unit 45.

Fluorescence produced at the examination object as a result of being irradiated with a laser beam is collected by the objective lens 53, returns along the optical path of the laser beam, and passes through the wavefront-restoring element 51. Thereafter, the fluorescence is returned by the plane mirror 45A of the optical-path-length changing unit 45 via the reflection mirror 49, the pair of second intermediate-image forming lenses 47, the half mirror 41, and the intermediate-image forming lens 43.

After passing through the wavefront-disturbing element 37 via the intermediate-image forming lens 43, the half mirror 41, and the pair of first intermediate-image forming lenses 39, the fluorescence returned by the plane mirror 45A is focused by the image-forming lens 55 via the galvanometer mirror 35 and the dichroic mirror 33 and is then detected by the photodetector 29 after passing through the pinhole 27.

After the disturbance is imparted to the wavefront of this fluorescence as a result of the fluorescence passing through the wavefront-restoring element 51, the fluorescence forms an intermediate image at the plane mirror 45A of the optical-path-length changing unit 45, hence causing the intermediate image to become unclear. Therefore, even if a foreign object exists on the surface of the plane mirror 45A, the image of the foreign object can be prevented from overlapping the intermediate image. Furthermore, for the fluorescence after forming the unclear intermediate image, the wavefront disturbance imparted by the wavefront-restoring element 51 is canceled out as a result of the fluorescence passing through the wavefront-disturbing element 37. For this reason, an image that has been made clear can be formed at the pinhole 27, so that the fluorescence produced at the final-image forming position of the laser beam in the examination object can be detected efficiently by the photodetector 29.

Next, a phase-modulation-element adjustment system 1 according to this embodiment will be described.

The phase-modulation-element adjustment system 1 includes: a positional-relationship adjustment unit 3 that can adjust the relative positional relationship between the wavefront-disturbing element 37 and the wavefront-restoring element 51 of the laser-scanning confocal observation apparatus 100; a wavefront-aberration measurement unit 5 for measuring wavefront aberration of the laser beam from the CW laser 21 that has passed through the wavefront-disturbing element 37 and wavefront-restoring element 51; and a processor (control unit, calculation unit) 7 for controlling the positional-relationship adjustment unit 3.

Furthermore, the phase-modulation-element adjustment system 1 includes: a fiber coupler (light-splitting unit) 11 for splitting the laser beam emitted from the CW laser 21 between an observation laser beam guided to the collimating lens 31 by the optical fiber 23 (hereinafter, referred to as "the illumination light") and a laser beam for adjusting the phase-modulation element (hereinafter, referred to as "the reference light"); a single-mode optical fiber 13 (hereinafter, referred to simply as "the optical fiber 13") for guiding the reference light split off by the fiber coupler 11; and a collimating lens 15 for transforming the reference light guided by the optical fiber 13 into collimated light.

The positional-relationship adjustment unit 3 is connected to the wavefront-disturbing element 37. This positional-relationship adjustment unit 3 is configured to change the position of the wavefront-disturbing element 37 in a direction (Z direction) along the optical axis or in directions intersecting the optical axis (X direction, Y direction) and also to change the angle (θ) thereof about the optical axis, through the control of the processor 7.

The wavefront-aberration measurement unit 5 includes: a half mirror (multiplexing unit) 17 that multiplexes the reference light transformed into a collimated beam by the collimating lens 15 and the illumination light at a position closer to the examination-object side than the wavefront-disturbing element 37 and the wavefront-restoring element 51 are; and an image-capturing element (image-capturing unit) 19 for acquiring an image of interference fringes caused by an optical path difference between the illumination light and the reference light, both of which take the form of substantially collimated beams and are multiplexed by the half mirror 17. In conjunction with the CW laser 21 and the fiber coupler 11, the half mirror 17 and the image-capturing element 19 are configured to constitute an interferometer.

The half mirror 17, together with the objective lens 53, is mounted to a revolver, not shown in the figure. This half mirror 17 can be placed in the optical path of the illumination light, in place of the objective lens 53, by turning the revolver about a predetermined rotation axis.

The image-capturing element 19 is a two-dimensional image sensor, like a CCD (Charge Coupled Device) or a CMOS (Complementary Metal Oxide Semiconductor) device.

The processor 7 is configured to calculate the wavefront aberration of the illumination light that has passed through the wavefront-disturbing element 37 and the wavefront-restoring element 51 on the basis of interference fringes acquired by the image-capturing element 19. Furthermore, the processor 7 controls the positional-relationship adjustment unit 3 on the basis of the calculation result so as to reduce the wavefront aberration of the illumination light that has passed through the wavefront-disturbing element 37 and the wavefront-restoring element 51. The processor 7 makes extremely small wavefront aberration of the illumination light, for example, by adjusting the position and the angle of the wavefront-disturbing element 37 by means of the positional-relationship adjustment unit 3 so that the wavefront of the illumination light approximates a plane wave as much as possible.

Next, the phase-modulation-element adjustment method according to this embodiment will be described.

The phase-modulation-element adjustment method includes: a measurement step of measuring the wavefront aberration of a laser beam from the CW laser 21 that has passed through the wavefront-disturbing element 37 and the wavefront-restoring element 51; and an adjustment step of adjusting the relative positional relationship between the wavefront-disturbing element 37 and the wavefront-restoring element 51 so as to reduce the wavefront aberration measured in the measurement step.

Next, the phase-modulation-element adjustment system 1 with the above-described structure and the phase-modulation-element adjustment method will be described.

In order to adjust the phase modulation imparted by the wavefront-disturbing element 37 and the wavefront-restoring element 51 of the laser-scanning confocal observation apparatus 100 by means of the phase-modulation-element adjustment system 1 according to this embodiment, the half mirror 17 is first placed in the optical path in place of the objective lens 53, and the image-capturing element 19 is then placed in place of the examination object.

Subsequently, the laser beam emitted from the CW laser 21 is split by the fiber coupler 11 into the illumination light and the reference light. The illumination light split off by the fiber coupler 11 is guided by the optical fiber 23 to the image-forming optical system 25 and then passes through the half mirror 17 towards the image-capturing element 19 via the wavefront-disturbing element 37 and the wavefront-restoring element 51. Meanwhile, the reference light split off by the fiber coupler 11 is guided by the optical fiber 13 and is reflected by the half mirror 17 towards the image-capturing element 19 via the collimating lens 15.

By doing so, the illumination light and the reference light are multiplexed at the half mirror 17, and an image of interference fringes caused by interference between the illumination light and the reference light, which are in the form of substantially collimated beams, is acquired by the image-capturing element 19. Then, on the basis of the image of interference fringes acquired by the image-capturing element 19, the processor 7 calculates the wavefront aberration of the illumination light that has passed through the wavefront-disturbing element 37 and the wavefront-restoring element 51 (measurement step), and, on the basis of the wavefront aberration, the positional-relationship adjustment unit 3 is controlled.

In this case, if there is a shift in the positional relationship between the wavefront-disturbing element 37 and the wavefront-restoring element 51, the spatial disturbance imparted by the wavefront-disturbing element 37 to the wavefront of the illumination light cannot be cancelled out with high accuracy by the wavefront-restoring element 51, and neither can the spatial disturbance imparted by the wavefront-restoring element 51 to the fluorescence wavefront be cancelled out with high accuracy by the wavefront-disturbing element 37. If this is the case, the wavefront aberration of the illumination light that has passed through the wavefront-disturbing element 37 and the wavefront-restoring element 51 becomes large.

According to this embodiment, the position of the wavefront-disturbing element 37 in the XYZ directions and the angle 9 thereof about the optical axis are adjusted by the positional-relationship adjustment unit 3 so that the wavefront of the illumination light approximates a plane wave as much as possible (adjustment step), thereby significantly reducing wavefront aberration of the illumination light that passes through the wavefront-disturbing element 37 and the wavefront-restoring element 51.

Because of this, the spatial disturbance imparted by the wavefront-disturbing element 37 to the wavefront of illumination light is cancelled out with high accuracy by the wavefront-restoring element 51, so that the final image formed in and downstream of the wavefront-restoring element 51 can be made clearer. Furthermore, the spatial disturbance imparted by the wavefront-restoring element 51 to the fluorescence wavefront is cancelled out with high accuracy by the wavefront-disturbing element 37 to form a clear image at the pinhole 27, thus allowing the photodetector 29 to detect the fluorescence more efficiently.

When the focal position in the examination object is moved in the optical-axis direction with the optical-path-length changing unit 45, the intermediate image formed by the pair of second intermediate-image forming lenses 47 also moves by a large amount in the optical-axis direction. Even if the intermediate image overlaps the positions of the pair of second intermediate-image forming lenses 47, or if any other optical element exists within the range of the movement, as a result of the movement, it is possible to prevent an acquired image of a foreign object from overlapping the final image because the intermediate image is made unclear.

As described above, the phase-modulation-element adjustment system 1 and the phase-modulation-element adjustment method according to this embodiment can prevent the occurrence of the disadvantage that, if some optical element is placed in an intermediate-image position of the laser-scanning confocal observation apparatus 100 and also if a flaw, foreign object, or defect exists on the surface of, or in, the optical element, such a flaw, foreign object, or defect on/in the optical element overlaps the intermediate image and is eventually formed as a part of the final image. For this reason, a sharp image of the examination object can be acquired by means of the laser-scanning confocal observation apparatus 100.

Second Embodiment

A phase-modulation-element adjustment system 101 and a phase-modulation-element adjustment method according to a second embodiment of the present invention will now be described.

Figure 2:
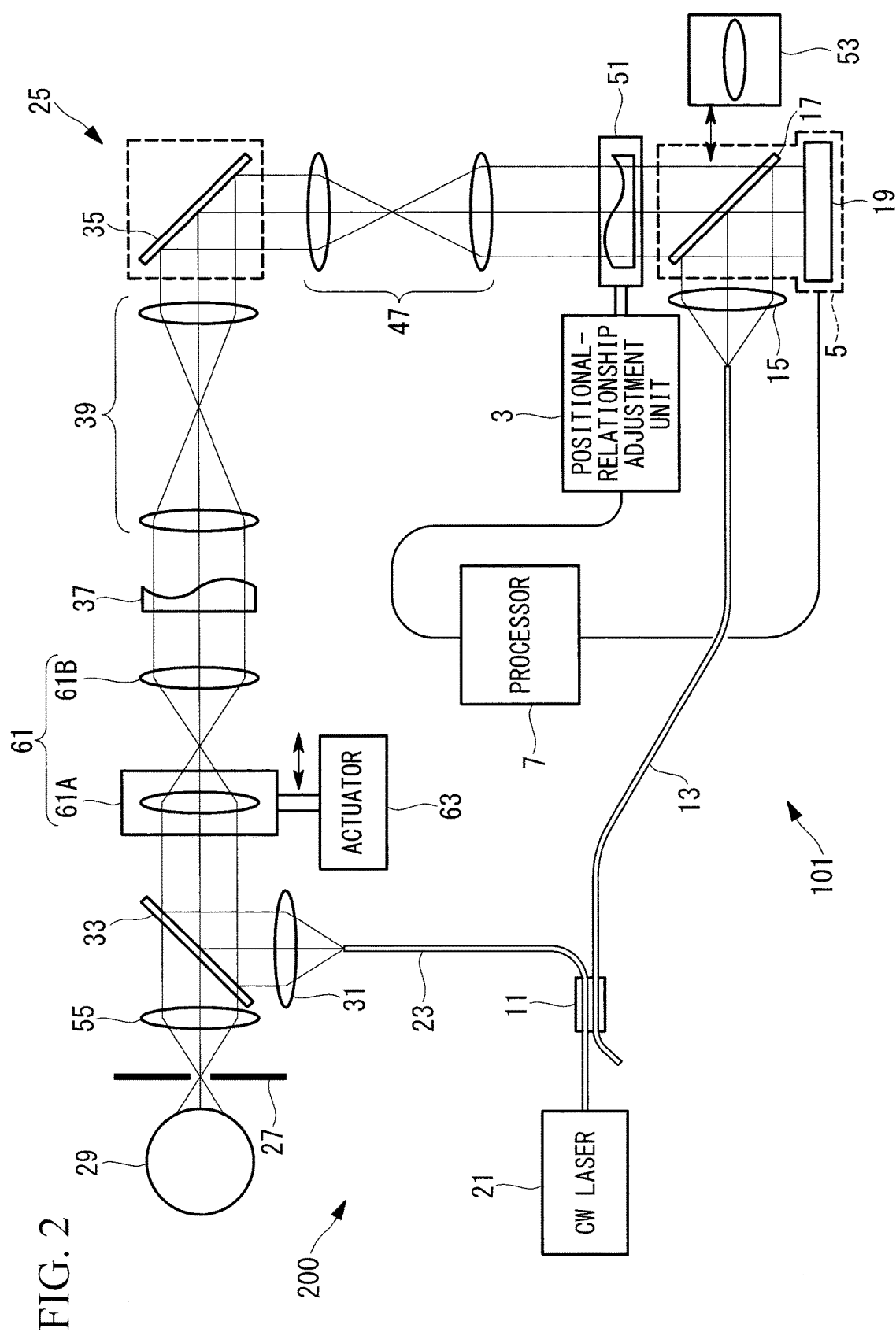
FIG. 2 is a schematic diagram depicting a phase-modulation-element adjustment system according to a second embodiment of the present invention.

As shown in FIG. 2, the phase-modulation-element adjustment system 101 according to this embodiment differs from the first embodiment in that the positional-relationship adjustment unit 3 adjusts the position and the angle of the wavefront-restoring element 51. The phase-modulation-element adjustment method is the same as in the first embodiment.

In the following description, parts in common with the structures of the phase-modulation-element adjustment system 1 and the phase-modulation-element adjustment method according to the first embodiment are denoted with the same reference signs, and a description thereof will be omitted.

This embodiment will be described by way of an example where the phase-modulation-element adjustment system 101 and the phase-modulation-element adjustment method are used for a laser-scanning confocal observation apparatus (microscope apparatus) 200, as shown in FIG. 2.

First, the laser-scanning confocal observation apparatus 200 will be described.

In the laser-scanning confocal observation apparatus 200, the image-forming optical system 25 includes: a collimating lens 31; a dichroic mirror 33; an intermediate-image forming optical system (image-forming lens) 61 that focuses the laser beam deflected by the dichroic mirror 33 to form an intermediate image; an actuator (optical-path-length changing unit) 63 for changing the focal position in the examination object; a wavefront-disturbing element 37 for imparting a phase modulation to the wavefront of the laser beam that has passed through the intermediate-image forming optical system 61; a pair of first intermediate-image forming lenses 39; a galvanometer mirror 35; a pair of second intermediate-image forming lenses 47 that focus the laser beam scanned by the galvanometer mirror 35 to form an intermediate image; a wavefront-restoring element 51 for imparting a phase modulation to the wavefront of the laser beam focused by the pair of second intermediate-image forming lenses 47; and an objective lens 53.

The actuator 63 is configured to move one of the lenses 61A and 61B, e.g., the lens 61A, in the optical-axis direction thereof, i.e. the lenses 61A and 61B constituting the intermediate-image forming optical system 61. The focal position in the examination object can be moved in the optical-axis direction by moving the lens 61A in the optical-axis direction with the use of the actuator 63.

In the laser-scanning confocal observation apparatus 200 with the above-described structure, a laser beam produced in the CW laser 21 is guided by the optical fiber 23 and passes through the wavefront-disturbing element 37 via the collimating lens 31, the dichroic mirror 33, and the intermediate-image forming optical system 61. Then, the laser beam passes through the wavefront-restoring element 51 via the pair of first intermediate-image forming lenses 39, the galvanometer mirror 35, and the pair of second intermediate-image forming lenses 47 and is then radiated onto the examination object by the objective lens 53.

Here, through the wavefront-disturbing element 37, disturbance is imparted to the wavefront of the laser beam, causing the intermediate image to become unclear, and therefore, even if a foreign object is present on the intermediate-image forming plane, it is possible to prevent the image of the foreign object from overlapping the intermediate image. Furthermore, when the laser beam after forming the unclear intermediate image passes through the wavefront-restoring element 51, the wavefront disturbance imparted by the wavefront-disturbing element 37 is cancelled out, and therefore, the final image that has been made clear can be formed in the examination object.

The fluorescence produced in the examination object as a result of being irradiated with the laser beam is collected by the objective lens 53, returns along the optical path of the laser beam, and passes through the wavefront-restoring element 51. Then, after passing through the wavefront-disturbing element 37 via the pair of second intermediate-image forming lenses 47, the galvanometer mirror 35, and the pair of first intermediate-image forming lenses 39, the fluorescence is focused by the image-forming lens 55 via the intermediate-image forming optical system 61 and the dichroic mirror 33 and is then detected by the photodetector 29 after passing through the pinhole 27.

Here, because the disturbance is imparted to the fluorescence wavefront through the wavefront-restoring element 51 and the intermediate image is made unclear, it is possible to prevent the image of a foreign object from overlapping the intermediate image even if the foreign object is present on the intermediate-image plane. Furthermore, for the fluorescence after forming the unclear intermediate image, the wavefront disturbance imparted by the wavefront-restoring element 51 is canceled out as a result of the fluorescence passing through the wavefront-disturbing element 37. For this reason, an image that has been made clear can be formed at the pinhole 27, so that the fluorescence can be detected efficiently by the photodetector 29.

When the focal position in the examination object is moved in the optical-axis direction by moving the lens 61A in the optical-axis direction thereof by the use of the actuator 63, the intermediate images formed by the pair of first intermediate-image forming lenses 39 and the pair of second intermediate-image forming lenses 47 also move by a large amount in the optical-axis direction. Even if the intermediate images overlap the positions of the pair of first intermediate-image forming lenses 39 and the pair of second intermediate-image forming lenses 47 or any other optical element exists within the range of the movement as a result of the movement, it is possible to prevent an acquired image of a foreign object from overlapping the final image because the intermediate images are made unclear.

Next, the phase-modulation-element adjustment system 101 according to this embodiment will be described.

The positional-relationship adjustment unit 3 is configured to change the position of the wavefront-restoring element 51 in a direction (Z direction) along the optical axis or in directions intersecting the optical axis (X direction, Y direction), and also to change the angle (θ) thereof about the optical axis, through the control of the processor 7.

The operation of the phase-modulation-element adjustment system 101 with the above-described structure and the phase-modulation-element adjustment method will be described.

In order to adjust the phase modulation imparted by the wavefront-disturbing element 37 and the wavefront-restoring element 51 of the laser-scanning confocal observation apparatus 200 by means of the phase-modulation-element adjustment system 101 according to this embodiment, the half mirror 17 is first placed in the optical path in place of the objective lens 53, and the image-capturing element 19 is then placed in place of the examination object. Then, the laser beam emitted from the CW laser 21 is split by the fiber coupler 11 into the illumination light and the reference light.

The illumination light split off by the fiber coupler 11 is guided by the optical fiber 23 to the image-forming optical system 25 and then passes through the half mirror 17 towards the image-capturing element 19 via the wavefront-disturbing element 37 and the wavefront-restoring element 51. Meanwhile, the reference light split off by the fiber coupler 11 is guided by the optical fiber 13 and is reflected by the half mirror 17 towards the image-capturing element 19 via the collimating lens 15.

By doing so, the illumination light and the reference light are multiplexed in the half mirror 17, and an image of interference fringes caused by interference between the illumination light and the reference light, which are in the form of substantially collimated beams, is acquired by the image-capturing element 19. Then, on the basis of the image of interference fringes acquired by the image-capturing element 19, the processor 7 calculates the wavefront aberration of the illumination light that has passed through the wavefront-disturbing element 37 and the wavefront-restoring element 51 (measurement step), and, on the basis of the wavefront aberration, the positional-relationship adjustment unit 3 is controlled.

More specifically, the position of the wavefront-restoring element 51 in the XYZ directions and the angle θ thereof about the optical axis are adjusted by the positional-relationship adjustment unit 3 so that the wavefront of the illumination light approximates a plane wave as much as possible (adjustment step), thereby significantly reducing the wavefront aberration of the illumination light that passes through the wavefront-disturbing element 37 and the wavefront-restoring element 51.

Because of this, the spatial disturbance imparted by the wavefront-disturbing element 37 to the wavefront of illumination light is cancelled out with high accuracy by the wavefront-restoring element 51, so that the final image formed in and downstream of the wavefront-restoring element 51 can be made clearer. Furthermore, the spatial disturbance imparted by the wavefront-restoring element 51 to the fluorescence wavefront is cancelled out with high accuracy by the wavefront-disturbing element 37 to form a clear image at the pinhole 27, thus allowing the photodetector 29 to detect the fluorescence more efficiently.

Therefore, the phase-modulation-element adjustment system 101 and the phase-modulation-element adjustment method according to this embodiment afford advantages similar to those of the first embodiment.

Third Embodiment

Next, a phase-modulation-element adjustment system 1 and a phase-modulation-element adjustment method according to a third embodiment of the present invention will be described.

Figure 3:
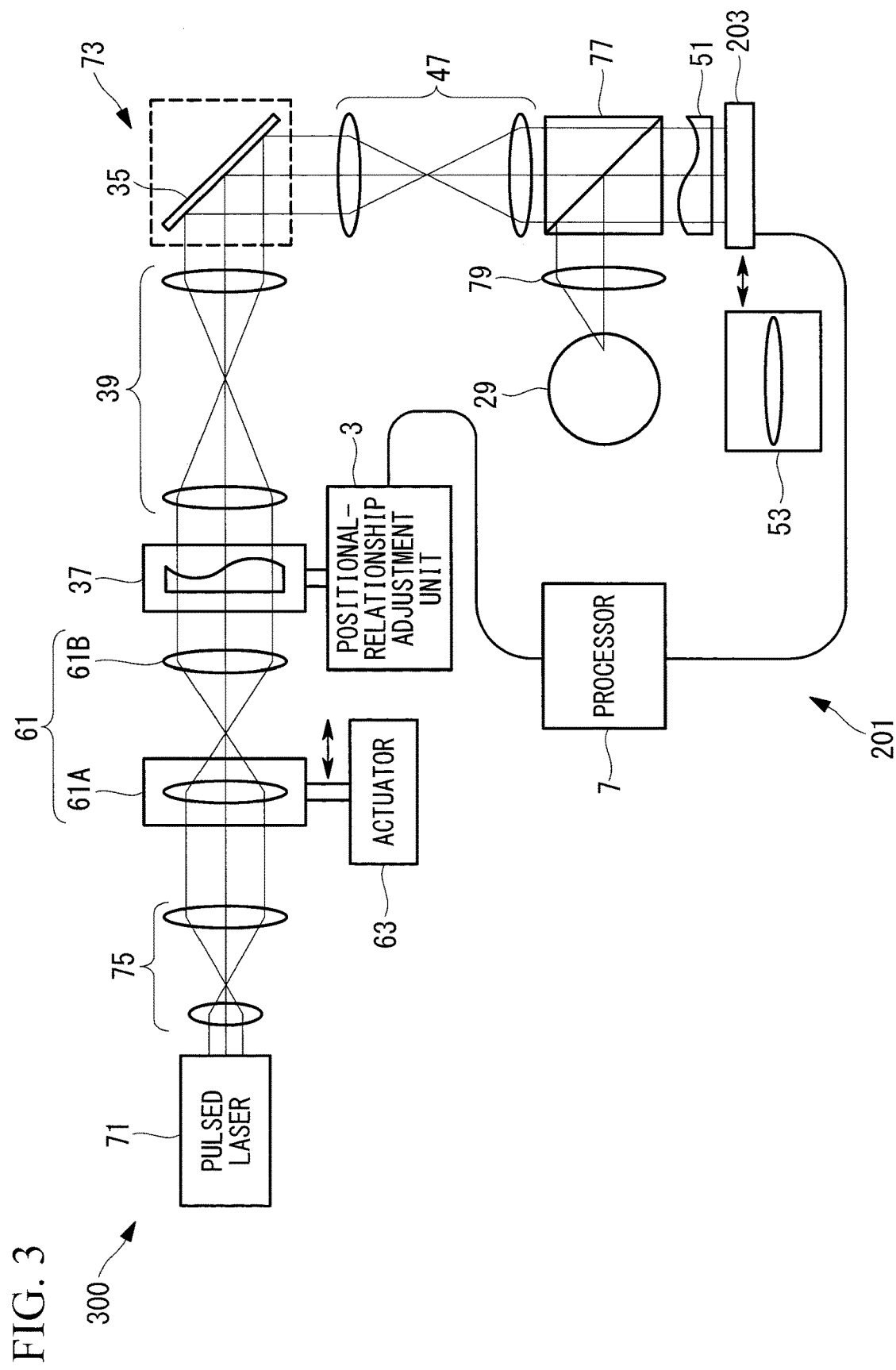
FIG. 3 is a schematic diagram depicting a phase-modulation-element adjustment system according to a third embodiment of the present invention.

As shown in FIG. 3, the phase-modulation-element adjustment system 201 according to this embodiment differs from the first embodiment and the second embodiment in that a Shack-Hartmann sensor 203 is provided as the wavefront-aberration measurement unit.

In the following description, parts in common with the structures of the phase-modulation-element adjustment systems 1 and 101 and the phase-modulation-element adjustment method according to the first and second embodiments are denoted with the same reference signs, and a description thereof will be omitted.

This embodiment is described by way of an example where the phase-modulation-element adjustment system 201 and the phase-modulation-element adjustment method are used for a laser-scanning multiphoton-excitation observation apparatus (microscope apparatus) 300, as shown in FIG. 3.

First, the laser-scanning multiphoton-excitation observation apparatus 300 will be described.

The laser-scanning multiphoton-excitation observation apparatus 300 includes: a pulsed laser (object) 71 for producing an ultra-short pulse laser beam (hereinafter, referred to simply as "the laser beam"); an image-forming optical system 73 that focuses the laser beam emitted from the pulsed laser 71 onto the examination object and that also collects the light from the examination object; and a photodetector 29 for detecting the fluorescence that is collected by the image-forming optical system 73 and that returns along the optical path of the laser beam.

The image-forming optical system 73 includes: a beam expander 75 for magnifying the beam diameter of the laser beam from the pulsed laser 71; an intermediate-image forming optical system 61; an actuator 63; a wavefront-disturbing element 37; a pair of first intermediate-image forming lenses 39; a galvanometer mirror 35; a pair of second intermediate-image forming lenses 47; a half mirror 77; a wavefront-restoring element 51; an objective lens 53; and a focusing lens 79 for focusing the fluorescence that is produced in the examination object, collected by objective lens 53, and returns along the optical path of the laser beam.

While transmitting the laser beam from the pair of second intermediate-image forming lenses 47, the half mirror 77 deflects, towards the focusing lens 79, the fluorescence that returns from the examination object along the optical path of the laser beam via the objective lens 53 and the wavefront-restoring element 51.

In the laser-scanning multiphoton-excitation observation apparatus 300 with the above-described structure, after the beam diameter of the laser beam produced in the pulsed laser 71 has been magnified by the beam expander 75, the laser beam passes through the wavefront-disturbing element 37 via the intermediate-image forming optical system 61 and is scanned two-dimensionally by the galvanometer mirror 35 via the pair of first intermediate-image forming lenses 39. Then, the laser beam passes through the wavefront-restoring element 51 via the pair of second intermediate-image forming lenses 47 and the half mirror 77 and is radiated by the objective lens 53 onto the examination object.

The fluorescence produced in the examination object as a result of being irradiated with the laser beam is collected by the objective lens 53 and passes through the wavefront-restoring element 51, is deflected by the half mirror 77, is focused by the focusing lens 79, and is detected by the photodetector 29.

Here, through the wavefront-disturbing element 37, the disturbance is imparted to the wavefront of the laser beam, causing the intermediate image to become unclear, and therefore, even if a foreign object is present on the intermediate-image forming plane, it is possible to prevent the image of the foreign object from overlapping the intermediate image. Furthermore, when the laser beam after forming the unclear intermediate image passes through the wavefront-restoring element 51, the wavefront disturbance imparted by the wavefront-disturbing element 37 is cancelled out, and therefore, the final image that has been made clear can be formed on the examination object.

Next, the phase-modulation-element adjustment system 201 according to this embodiment will be described.

The phase-modulation-element adjustment system 201 includes: a positional-relationship adjustment unit 3 capable of changing the position of the wavefront-disturbing element 37 in a direction (Z direction) along the optical axis and directions intersecting the optical axis (X direction, Y direction), as well as the angle (θ) thereof about the optical axis; a laser Shack-Hartmann sensor 203 for measuring the wavefront aberration of the laser beam in the form of a substantially collimated beam; and a processor 7.

The Shack-Hartmann sensor 203, together with the objective lens 53, is mounted on a revolver, not shown in the figure, and can be placed in the optical path of the laser beam, in place of the objective lens 53, by turning the revolver about a predetermined rotation axis.

This Shack-Hartmann sensor 203 includes, for example, a microlens array, an image-capturing element, and an analytical calculation unit (none of them are shown in the figure). This Shack-Hartmann sensor 203 is configured to measure the wavefront aberration by acquiring, with the image-capturing element, images of focal spots of the light beam entering the microlens array and by analyzing, with the analytical calculation unit, the focal position of each of the focal spots on the basis of the acquired image data.

On the basis of the wavefront aberration of the illumination light measured by the Shack-Hartmann sensor 203, the processor 7 controls the positional-relationship adjustment unit 3 so that the wavefront aberration of the illumination light is reduced.

Next, the phase-modulation-element adjustment method according to this embodiment will be described.

The phase-modulation-element adjustment method includes: a measurement step of measuring the wavefront aberration of the laser beam from the pulsed laser 71 that has passed through the wavefront-disturbing element 37 and the wavefront-restoring element 51; and an adjustment step of adjusting the relative positional relationship between the wavefront-disturbing element 37 and the wavefront-restoring element 51 so that the wavefront aberration measured in the measurement step decreases.

The operation of the phase-modulation-element adjustment system 201 with the above-described structure and the phase-modulation-element adjustment method will now be described.

In order to adjust the phase modulation imparted by the wavefront-disturbing element 37 and the wavefront-restoring element 51 of the laser-scanning multiphoton-excitation observation apparatus 300 using the phase-modulation-element adjustment system 201 according to this embodiment, the Shack-Hartmann sensor 203 is first placed in place of the objective lens 53, and a laser beam is produced from the pulsed laser 71.

The laser beam emitted from the pulsed laser 71 passes through the wavefront-disturbing element 37 and the wavefront-restoring element 51 of the image-forming optical system 73 in the same manner as in the above-described multiphoton excitation observation. Thereafter, the laser beam is received by the Shack-Hartmann sensor 203, and the wavefront aberration of the illumination light is calculated (measurement step).

Next, on the basis of the wavefront aberration of the illumination light measured by the Shack-Hartmann sensor 203, the positional-relationship adjustment unit 3 is controlled by the processor 7. More specifically, the position of the wavefront-disturbing element 37 in the XYZ directions and the angle θ thereof about the optical axis are adjusted by the positional-relationship adjustment unit 3 so that the wavefront of the illumination light approximates a plane wave as much as possible (adjustment step), thereby significantly reducing the wavefront aberration of the laser beam from the pulsed laser 71 that has passed through the wavefront-disturbing element 37 and the wavefront-restoring element 51.

Because of this, the spatial disturbance imparted by the wavefront-disturbing element 37 to the wavefront of the laser beam is cancelled out with high accuracy by the wavefront-restoring element 51, so that the final image formed in and downstream of the wavefront-restoring element 51 becomes clearer.

As described above, according to the phase-modulation-element adjustment system 201 and the phase-modulation-element adjustment method of this embodiment, the wavefront aberration of light can be measured, without having to use an interferometer, by employing the Shack-Hartmann sensor 203 as the wavefront-aberration measurement unit. Therefore, the system structure can be made simple and compact.

Fourth Embodiment

Next, a phase-modulation-element adjustment system 1 and a phase-modulation-element adjustment method according to a fourth embodiment of the present invention will be described.

Figure 4:
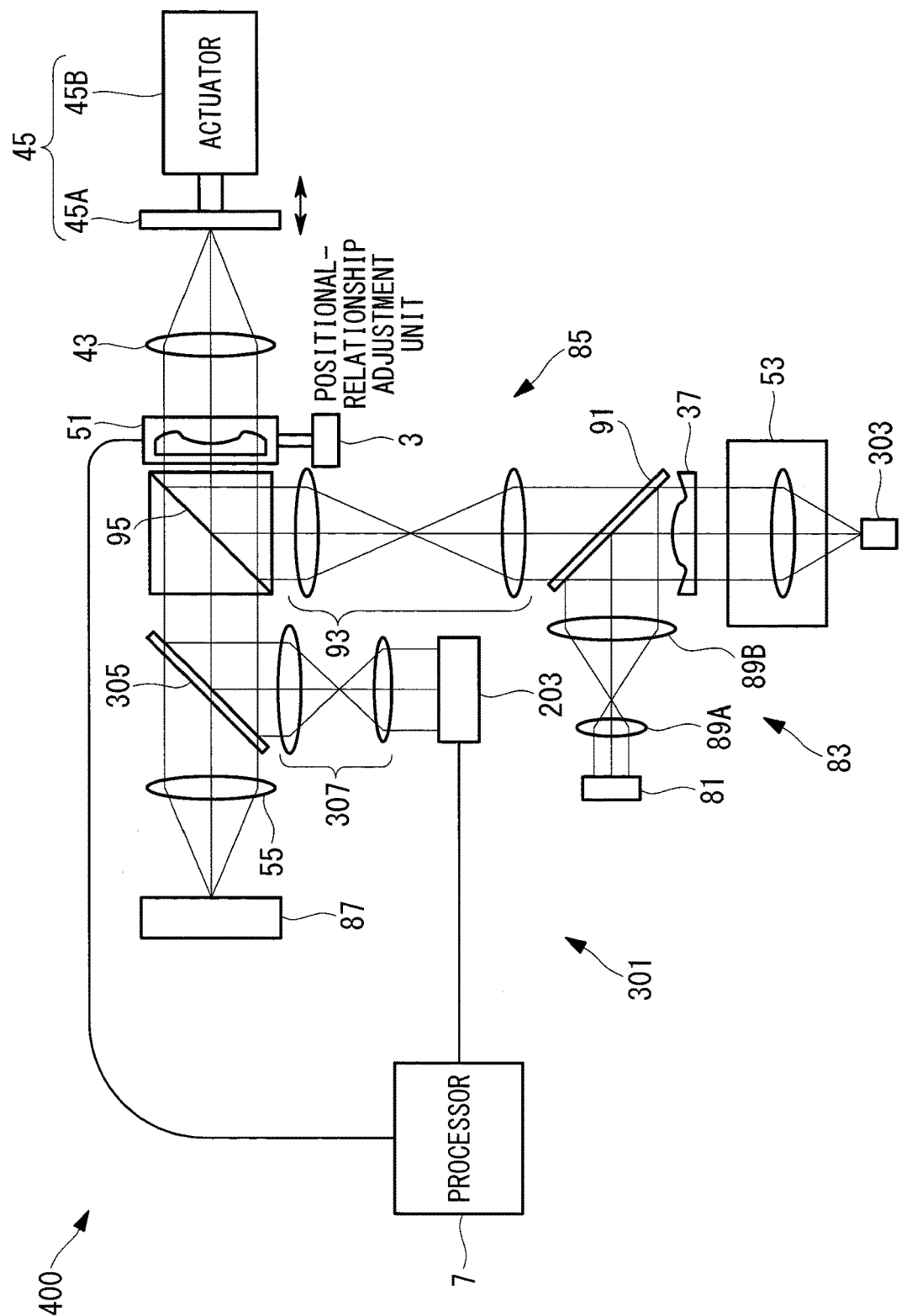
FIG. 4 is a schematic diagram depicting a phase-modulation-element adjustment system according to a fourth embodiment of the present invention.

As shown in FIG. 4, a phase-modulation-element adjustment system 301 according to this embodiment differs from the first embodiment, the second embodiment, and the third embodiment in that it is provided with a light source 303 for producing a laser beam for phase adjustment and the Shack-Hartmann sensor (wavefront-aberration measurement unit) 203 placed closer to the final-image side than the wavefront-disturbing element 37 and the wavefront-restoring element 51 are.

In the following description, parts in common with the structures of the phase-modulation-element adjustment systems 1, 101 and 201 and the phase-modulation-element adjustment method according to the first, second, and third embodiments are denoted with the same reference signs, and a description thereof will be omitted.

This embodiment will be described by way of an example where the phase-modulation-element adjustment system 301 and the phase-modulation-element adjustment method are used for a fluorescence microscope (microscope apparatus) 400 as shown in FIG. 4.

First, the fluorescence microscope 400 will be described.

The fluorescence microscope 400 includes: a light-source-for-illumination (object) 81 for producing non-coherent illumination light; an illumination optical system 83 for illuminating the examination object (object) with the illumination light emitted from the light-source-for-illumination 81; an imaging optical system 85 for collecting the light from the examination object; and an image-capturing element 87, like a CCD or a CMOS, that acquires an image of the light collected by the imaging optical system 85.

The illumination optical system 83 includes: illumination lenses 89A and 89B for focusing the illumination light from the light-source-for-illumination 81; and an objective lens 53 for irradiating the examination object with the illumination light focused by the illumination lenses 89A and 89B. This illumination optical system 83 is a so-called Koehler illumination system, and the illumination lenses 89A and 89B are placed so that the light emission surface of the light-source-for-illumination 81 and the pupil surface of the objective lens 53 are conjugate with each other.

The imaging optical system 85 includes: the above-described objective lens (image-forming lens) 53 for collecting the observation light (e.g., reflected light) emitted from the examination object; a wavefront-disturbing element 37 for imparting a phase modulation to the wavefront of the observation light collected by the objective lens 53; a first beam splitter 91 for splitting off the observation light the wavefront of which has been subjected to phase modulation from the optical path of the illumination light coming from the light-source-for-illumination 81; a pair of intermediate-image forming lenses (image-forming lenses) 93 placed so as to be separated from each other in the optical-axis direction; a second beam splitter 95 for deflecting by 90° the observation light that has passed through the pair of intermediate-image forming lenses 93; an intermediate-image forming lens (image-forming lens) 43 that focuses the observation light deflected by the second beam splitter 95 to form an intermediate image; an optical-path-length changing unit 45 placed on the intermediate-image forming plane resulting from the intermediate-image forming lens 43; a wavefront-restoring element 51 placed between the second beam splitter 95 and the intermediate-image forming lens 43; and an image-forming lens 55 that focuses the observation light having passed through the wavefront-restoring element 51 and the second beam splitter 95 to form a final image.

The image-capturing element 87 is provided with an image-capturing plane (not shown in the figure) placed in the image-forming position of the final image resulting from the image-forming lens 55 and is configured to acquire a two-dimensional image of the examination object by acquiring an image of the observation light incident upon the image-capturing plane.

The wavefront-disturbing element 37 is placed in the vicinity of the pupil position of the objective lens 53. This wavefront-disturbing element 37 is configured to impart the necessary wavefront disturbance by transmitting once the observation light from the examination object.

The wavefront-restoring element 51 is placed in the vicinity of the pupil position of the pair of second intermediate-image forming lenses 47. This wavefront-restoring element 51 is configured to impart, to the wavefront of the observation light, a phase modulation that would cancel out the wavefront disturbance imparted by the wavefront-disturbing element 37 by transmitting the observation light deflected by the second beam splitter 95 and the observation light reflected by the optical-path-length changing unit 45, twice in a round trip.

The fluorescence microscope 400 with the above-described structure irradiates the examination object with the illumination light emitted from the light-source-for-illumination 81 by means of the illumination optical system 83. As a result of the illumination light being radiated, the observation light returning from the examination object is collected by the objective lens 53, passes through the wavefront-disturbing element 37 a first time, and is deflected by the second beam splitter 95 via the first beam splitter 91 and the pair of intermediate-image forming lenses 93.

The observation light deflected by the second beam splitter 95 passes through the wavefront-restoring element 51 and is reflected by the plane mirror 45A of the optical-path-length changing unit 45 via the intermediate-image forming lens 43. Then, the observation light passes through the wavefront-restoring element 51 a second time via the intermediate-image forming lens 43 and is focused by the image-forming lens 55 after passing through the second beam splitter 95. By doing so, a final image formed by the image-forming lens 55 is acquired by the image-capturing element 87.

Here, an intermediate image formed by the intermediate-image forming lens 43 is formed in the vicinity of the plane mirror 45A of the optical-path-length changing unit 45, and this intermediate image becomes unclear due to the wavefront disturbance, which was imparted through the wavefront-disturbing element 37 and has remained after being partially canceled out when passing through the wavefront-restoring element 51 a first time. Then, the observation light after forming the unclear intermediate image is collected by the intermediate-image forming lens 43, and thereafter passes through the wavefront-restoring element 51 a second time, thereby causing the wavefront disturbance to be cancelled out.

Consequently, even if a foreign object, such as a flaw or dust, exists on the surface of the plane mirror 45A, not only is it possible to prevent an acquired image of the foreign object from overlapping the final image but also a sharp image of the examination object can be acquired.

Next, the phase-modulation-element adjustment system 301 according to this embodiment will be described.

The phase-modulation-element adjustment system 301 includes: a light source 303 for causing a laser beam from the examination-object side to be incident upon the wavefront-disturbing element 37 and the wavefront-restoring element 51; a positional-relationship adjustment unit 3 that is capable of changing the position of the wavefront-restoring element 51 in the XYZ directions and the angle θ thereof about the optical axis; a reflection mirror 305 for reflecting the laser beam from the light source 303; a group of relay lenses 307 for relaying the laser beam reflected by the reflection mirror 305; a Shack-Hartmann sensor 203 for measuring the wavefront aberration of the substantially collimated laser beam relayed by the group of relay lenses 307; and a processor 7.

Next, the phase-modulation-element adjustment method according to this embodiment will be described.

The phase-modulation-element adjustment method includes: a measurement step of measuring the wavefront aberration of the laser beam from the light source (object) 303 that has passed through the wavefront-disturbing element 37 and the wavefront-restoring element 51; and an adjustment step of adjusting the relative positional relationship between the wavefront-disturbing element 37 and the wavefront-restoring element 51 so as to decrease the wavefront aberration measured in the measurement step.

The operation of the phase-modulation-element adjustment system 301 with the above-described structure and the phase-modulation-element adjustment method will be described.

In order to adjust the phase modulation imparted by the wavefront-disturbing element 37 and the wavefront-restoring element 51 of the fluorescence microscope 400 using the phase-modulation-element adjustment system 301 according to this embodiment, the light source 303 is first placed in place of the examination object, and a laser beam is produced from the light source 303.

The laser beam emitted from the light source 303 is collected by the objective lens 53, passes through the wavefront-disturbing element 37, and is deflected by the second beam splitter 95 via the first beam splitter 91 and the pair of intermediate-image forming lenses 93. The laser beam deflected by the second beam splitter 95 is focused by the intermediate-image forming lens 43 after passing through the wavefront-restoring element 51 and is then reflected by the optical-path-length changing unit 45.

The laser beam reflected by the optical-path-length changing unit 45 passes through the wavefront-restoring element 51 via the intermediate-image forming lens 43 and is received by the Shack-Hartmann sensor 203 via the second beam splitter 95, the reflection mirror 305, and the group of relay lenses 307, and then the wavefront aberration of the laser beam is calculated (measurement step).

Subsequently, on the basis of the wavefront aberration of the laser beam measured by the Shack-Hartmann sensor 203, the positional-relationship adjustment unit 3 is controlled by the processor 7. More specifically, the position of the wavefront-restoring element 51 in the XYZ directions and the angle θ thereof about the optical axis are adjusted by the positional-relationship adjustment unit 3 so that the wavefront of the laser beam approximates a plane wave as much as possible (adjustment step), thereby significantly reducing the wavefront aberration of the laser beam from the light source 303 that has passed through the wavefront-disturbing element 37 and the wavefront-restoring element 51.

Because of this, the spatial disturbance imparted by the wavefront-disturbing element 37 on the wavefront of observation light is cancelled out with high accuracy by the wavefront-restoring element 51, so that the final image formed in and downstream of the wavefront-restoring element 51 becomes clearer.

As described above, according to the phase-modulation-element adjustment system 301 and the phase-modulation-element adjustment method of this embodiment, when the wavefront aberration of the laser beam from the light source 303 that has passed through the wavefront-disturbing element 37 and the wavefront-restoring element 51 is to be measured, it is not necessary to take the trouble of removing from the optical path the objective lens 53 for collecting the light from the examination object. Furthermore, the relative positional relationship between the wavefront-disturbing element 37 and wavefront-restoring element 51, taking account of the influence by the aberration of the objective lens 53, can be adjusted.

Although the embodiments of the present invention have been described in detail with reference to the drawings, the specific structure is not limited to those of these embodiments but includes design changes etc. that do not depart from the spirit of the present invention. The present invention is not limited to the invention applied to each of the above-described embodiments but can be applied to, for example, embodiments in which these embodiments are appropriately combined and is not particularly limited.

In addition, although the position and the angle of either one of the wavefront-disturbing element 37 and the wavefront-restoring element 51 are adjusted in each of the above-described embodiments, the position and the angle of, for example, the other one or both of the wavefront-disturbing element 37 and the wavefront-restoring element 51 may be adjusted.

Furthermore, although the processor 7 controlled the positional-relationship adjustment unit 3 so that the wavefront of illumination light approximates a plane wave to the maximum possible level in each of the above-described embodiments, the positional-relationship adjustment unit 3 may be controlled so that the wavefront of illumination light approximates a spherical wave to the maximum possible level by, for example, changing the positions of the image-capturing element 19 and the Shack-Hartmann sensor 203.

As a result, the above-described embodiments lead to the following aspects.

A first aspect of the present invention is a phase-modulation-element adjustment system including: a positional-relationship adjustment unit that is used for a microscope apparatus including a plurality of image-forming lenses for forming a final image and at least one intermediate image and two phase-modulation elements being placed at positions between which any of the intermediate images formed by the image-forming lenses is disposed and having opposite phase characteristics to each other and that is capable of adjusting a relative positional relationship between the two phase-modulation elements; a wavefront-aberration measurement unit for measuring a wavefront aberration of light that has come from an object and that has passed through the two phase-modulation elements; and a control unit for controlling the positional-relationship adjustment unit so as to decrease the wavefront aberration measured by the wavefront-aberration measurement unit.

In the microscope apparatus, the final image is formed by focusing the light incident upon the image-forming lenses from the object side. Furthermore, through one of the phase-modulation elements placed closer to the object side than one of the intermediate images is, phase modulation that would produce spatial disturbance is imparted to the light wavefront, thereby causing the formed intermediate image to become blurred. In addition, as a result of the light that has formed an intermediate image passing through the other of the phase-modulation elements, a phase adjustment that would cancel out the spatial disturbance on the wavefront imparted by the one of the phase-modulation elements is applied.

According to this aspect, the positional-relationship adjustment unit is controlled by the control unit to adjust a relative positional relationship between the two phase-modulation elements, thereby decreasing the wavefront aberration, measured by the wavefront-aberration measurement unit, of the light that has come from the object and that has passed through the two phase-modulation elements. Because of this, the spatial disturbance imparted to the light wavefront by the one of the phase-modulation elements is canceled out with high accuracy by the other of the phase-modulation elements, and the final image formed in and downstream of the other of the phase-modulation elements becomes clear. Therefore, even if some optical element is placed in an intermediate-image position and a flaw, foreign object, defect, and so forth are present on the surface of or in the optical element, it is possible to prevent the occurrence of a disadvantage in that the flaw, foreign object, defect, and so forth of the optical element overlap the intermediate image and are eventually formed as a part of the final image.

In the above-described aspect, the positional-relationship adjustment unit may change at least one of a position of at least one of the two phase-modulation elements in a direction along an optical axis, a position thereof in a direction intersecting the optical axis, and an angle thereof about the optical axis.

With the above-described structure, the relative positional relationship between the two phase-modulation elements can be adjusted with high accuracy.

In the above-described aspect, the wavefront-aberration measurement unit may be placed at a position farther from the object than the two phase-modulation elements are.

With the above-described structure, wavefront aberration of the light that has come from the object and that has passed through the two phase-modulation elements can be measured without employing a complicated structure.

In the above-described aspect, a light source causing light from the object side to be incident on the two phase-modulation elements may be provided, and the wavefront-aberration measurement unit may be placed closer to the final-image side than the two phase-modulation elements are.

With the above-described structure, when the wavefront aberration of the light that has come from the object and that has passed through the two phase-modulation elements is to be measured, it is not necessary to take the trouble of removing from the optical path the image-forming lens, namely, the objective lens for collecting the light from the object. Furthermore, the positional relationship between the two phase-modulation elements, counting the influence by aberration of the objective lens, can be adjusted.

In the above-described aspect, the wavefront-aberration measurement unit may include: a light-splitting unit for splitting the light into illumination light for observation with the microscope apparatus and reference light for adjusting the phase-modulation elements; a multiplexing unit for multiplexing the illumination light made to pass through the two phase-modulation elements and the reference light not made to pass through the two phase-modulation elements; an image-capturing unit for acquiring an image of interference fringes caused by an optical path difference between the illumination light and the reference light multiplexed by the multiplexing unit; and a calculation unit for calculating the wavefront aberration on the basis of the image of interference fringes acquired by the image-capturing unit.

With the above-described structure, the wavefront aberration of the light can be measured easily and with high accuracy by configuring an interferometer of commonly available members.

In the above-described aspect, the wavefront-aberration measurement unit may be a Shack-Hartmann sensor.

With the above-described structure, the wavefront aberration of the light can be measured without using an interferometer. Therefore, the system structure can be made simple and compact.

A second aspect of the present invention is a phase-modulation-element adjustment method of a microscope apparatus, wherein a final image is formed by causing a first phase-modulation element to impart a spatial disturbance to a wavefront of light that comes from an object and that forms an intermediate image and by causing a second phase-modulation element to cancel out the spatial disturbance on the wavefront of the light that has formed the intermediate image, the method including: a measurement step of measuring wavefront aberration of the light that has from the object and that has passed through the two phase-modulation elements; and an adjustment step of adjusting a relative positional relationship between the two phase-modulation elements so as to decrease the wavefront aberration measured in the measurement step.

According to this aspect, on the basis of the wavefront aberration, measured in the measurement step, of the light that has come from the object and that has passed through the two phase-modulation elements, the relative positional relationship between the two phase-modulation elements is adjusted in the adjustment step, and the wavefront aberration of the light that has come from the object and that has passed through the two phase-modulation element is decreased, thereby allowing the second phase-modulation element to cancel out with high accuracy the spatial disturbance imparted to the light wavefront by the first phase-modulation element. Because of this, even if some optical element is placed in an intermediate-image position and a flaw, foreign object, defect, and so forth are present on the surface of or in the optical element, it is possible to prevent the occurrence of a disadvantage in that the flaw, foreign object, defect, and so forth of the optical element overlap the intermediate image and are eventually formed as a part of the final image, thereby making it possible to acquire a clear final image.

The present invention affords an advantage in that even if an intermediate image is formed at a position coinciding with an optical element, a flaw, foreign object, defect, and so forth of the optical element are prevented from overlapping the intermediate image, thereby acquiring a clear final image.

REFERENCE SIGNS LIST 1, 101, 201, 301 Phase-modulation-element adjustment system
3 Positional-relationship adjustment unit
5 Wavefront-aberration measurement unit
7 Processor (control unit, calculation unit)
11 Fiber coupler (light-splitting unit)
17 Half mirror (multiplexing unit)
19 Image-capturing element (image-capturing unit)
21 CW laser (object)
37 Wavefront-disturbing element (phase-modulation element)
39 Pair of first intermediate-image forming lenses (image-forming lens)
43 Intermediate-image forming lens (image-forming lens)
47 Pair of second intermediate-image forming lenses (image-forming lens)
51 Wavefront-restoring element (phase-modulation element)
53 Objective lens (image-forming lens)
55 Image-forming lens
61 Intermediate-image forming optical system (image-forming lens)
93 Pair of intermediate-image forming lenses (image-forming lens)
100, 200 Laser-scanning confocal observation apparatus (microscope apparatus)
203 Shack-Hartmann sensor (wavefront-aberration measurement unit)
300 Laser-scanning multiphoton-excitation observation apparatus (microscope apparatus)
303 Light source
400 Fluorescence microscope (microscope apparatus)

The invention claimed is:

1. A phase-modulation-element adjustment system comprising:
a positional-relationship adjustment unit that is used for a microscope apparatus including a plurality of image-forming lenses for forming a final image and at least one intermediate image and two phase-modulation elements being placed at positions between which any of the intermediate images formed by the image-forming lenses is disposed and having opposite phase characteristics to each other and that is capable of adjusting a relative positional relationship between the two phase-modulation elements;
a wavefront-aberration measurement unit for measuring a wavefront aberration of light that has come from an object and that has passed through the two phase-modulation elements; and
a control unit for controlling the positional-relationship adjustment unit so as to decrease the wavefront aberration measured by the wavefront-aberration measurement unit.

2. The phase-modulation-element adjustment system according to claim 1, wherein the positional-relationship adjustment unit changes at least one of a position of at least one of the two phase-modulation elements in a direction along an optical axis, a position thereof in a direction intersecting the optical axis, and an angle thereof about the optical axis.

3. The phase-modulation-element adjustment system according to claim 1, wherein the wavefront-aberration measurement unit is placed at a position farther from the object than the two phase-modulation elements are.

4. The phase-modulation-element adjustment system according to claim 1, comprising a light source causing light from the object side to be incident on the two phase-modulation elements,
wherein the wavefront-aberration measurement unit is placed closer to the final-image side than the two phase-modulation elements are.

5. The phase-modulation-element adjustment system according to claim 4, wherein the wavefront-aberration measurement unit includes:
a light-splitting unit for splitting the light into illumination light for observation with the microscope apparatus and reference light for adjusting the phase-modulation elements;
a multiplexing unit for multiplexing the illumination light made to pass through the two phase-modulation elements and the reference light not made to pass through the two phase-modulation elements;
an image-capturing unit for acquiring an image of interference fringes caused by an optical path difference between the illumination light and the reference light multiplexed by the multiplexing unit; and
a calculation unit for calculating the wavefront aberration on the basis of the image of interference fringes acquired by the image-capturing unit.

6. The phase-modulation-element adjustment system according to claim 1, wherein the wavefront-aberration measurement unit is a Shack-Hartmann sensor.

7. A phase-modulation-element adjustment method of a microscope apparatus,
wherein a final image is formed by causing a first phase-modulation element to impart a spatial disturbance to a wavefront of light that comes from an object and that forms an intermediate image and by causing a second phase-modulation element to cancel out the spatial disturbance on the wavefront of the light that has formed the intermediate image, the method comprising:
a measurement step of measuring a wavefront aberration of the light that has come from the object and that has passed through the two phase-modulation elements; and
an adjustment step of adjusting a relative positional relationship between the two phase-modulation elements so as to decrease the wavefront aberration measured in the measurement step.

* * * * *